(12) United States Patent
Yokoyama et al.

(10) Patent No.: US 7,666,900 B2
(45) Date of Patent: Feb. 23, 2010

(54) ABCA1 STABILIZER

(75) Inventors: Shinji Yokoyama, Nagoya (JP); Maki Tsujita, Nagoya (JP); Reijiro Arakawa, Hamura (JP); Tomoji Aotsuka, Hamura (JP)

(73) Assignee: Hykes Laboratories LLC, Aichi (JP)

( * ) Notice: Subject to any disclaimer, the term of this patent is extended or adjusted under 35 U.S.C. 154(b) by 365 days.

(21) Appl. No.: 10/586,338

(22) PCT Filed: Dec. 22, 2004

(86) PCT No.: PCT/JP2004/019717

§ 371 (c)(1),
(2), (4) Date: Aug. 15, 2006

(87) PCT Pub. No.: WO2005/067904

PCT Pub. Date: Jul. 28, 2005

(65) Prior Publication Data

US 2007/0161702 A1     Jul. 12, 2007

(30) Foreign Application Priority Data

Jan. 15, 2004   (JP) .............................. 2204-007955

(51) Int. Cl.
A01N 43/02   (2006.01)
A61K 31/38   (2006.01)
A01N 35/00   (2006.01)
A61K 31/10   (2006.01)
A01N 31/00   (2006.01)
A01N 27/00   (2006.01)
A61K 31/015  (2006.01)

(52) U.S. Cl. ...................... 514/430; 514/691; 514/712; 514/766; 514/824

(58) Field of Classification Search ................. 514/430, 514/691, 712, 766, 824
See application file for complete search history.

(56) References Cited

FOREIGN PATENT DOCUMENTS

| WO | 97/38681 | 10/1997 |
|---|---|---|
| WO | 01/77072 A2 | 10/2001 |
| WO | 02/04031 A1 | 1/2002 |

OTHER PUBLICATIONS

Matsuzawa Y, Yamashita S, Funahashi T, Yamamoto A, and Tarui S, "Selective reduction of cholesterol in HDL2 fraction by probucol in familial hypercholesterolemia and hyperHDL2 cholesterolemia with abnormal cholesteryl ester transfer," American Journal of Cardiology, Jul. 1988, 62(3), 66B-72B (abstract only).*

Tardif JC, Grégoire J, Lavoie MA, and L'Allier PL, "Pharmacologic prevention of both restenosis and atherosclerosis progression: AGI-1067, probucol, statins, folic acid and other therapies," Current Opinion in Lipidology, 14(6), 615-620.*

McLean, Larry et al., "Interactions of MDL 29,311 and Probucol Metabolites with Cholesteryl Esters" *Lipids*, vol. 29, No. 12, pp. 819 to 823 (1994).

Oram, J. F., "HDL Apolipoproteins and ABCA1: Partners in the Removal of Excess Cellular Cholesterol" *Arterioscler. Thromb. Vasc. Biol.*, vol. 23, No. 5, pp. 720 to 727 (2003).

* cited by examiner

*Primary Examiner*—San-ming Hui
*Assistant Examiner*—Paul Zarek
(74) *Attorney, Agent, or Firm*—Wenderoth, Lind & Ponack, LLP.

(57) ABSTRACT

To provide a pharmaceutically effective prophylactic/preventive agent for low-HDL cholesterolemia, focusing on an HDL-generating mechanism. The ABCA1 stabilizer of the present invention contains a bisphenol-type compound selected form probucol spiroquinone, probucol diphenoquinone, and probucol bisphenol as an effective ingredient. The ABCA1 stabilizer can continuously and stably express ABCA1 by a mechanism quite different from that of conventional processes, and thus is useful as prophylactic/preventive agent for low-HDL cholesterolemia or arteriosclerosis.

2 Claims, No Drawings

ABCA1 STABILIZER

FIELD OF THE INVENTION

The present invention relates to an ATP-binding cassette transport 1 (ABCA1) stabilizer. The ABCA1 stabilizer comprises, as an effective ingredient, a bisphenol-type compound selected from probucol spiroquinone (chemical name: 2,4,9,11-tetrakis(1,1-dimethylethyl)-14,14-dimethyl-13,15-dithiadispiro[5.0.5.3]pentadeca-1,4,8,11-tetraene-3,10-dione), probucol diphenoquinone (chemical name: 3,5,3',5'-tetra-t-butyl-4,4'-diphenoquinone), and probucol bisphenol (chemical name: 4,4'-dihydroxy-3,5,3',5'-tetra-t-butyldiphenyl). These bisphenol compounds are metabolites of probucol. The present invention further relates to a prophylactic/therapeutic agent comprising at least one ABCA1 stabilizer. The prophylactic/therapeutic agent is used for treating various diseases caused by a decrease in the ABCA1 expression, such as low-HDL (high-density lipoprotein) cholesterolemia and arteriosclerosis. Here, the ATP is an abbreviation for adenosine 5'-triphosphate that is involved in energy metabolism in vivo and plays an important role in acquisition and utilization of energy.

BACKGROUND OF THE INVENTION

Probucol is a compound having the chemical name 4,4'-(isopropylidenedithio)bis(2,6-di-t-butylphenol). Main functions of probucol are said to promote catabolism of cholesterol and its excretion into bile. Furthermore, probucol raises the catabolism rate of low-density lipoprotein (LDL)-cholesterol and reduces the serum total cholesterol level. Consequently, probucol is widely used as an agent for improving lipid metabolism in hyperlipidemia patients (including familial hypercholesterolemia and xanthoma patients).

However, probucol also has a clinically disadvantageous effect, i.e., reduces the cholesterol level in the HDL fraction (hereinafter sometimes referred to as "HDL-cholesterol"), unlike other lipid-lowering agents which have the reaction properties in LDL such as statins or fibrates (for example, refer to Non-Patent Documents 1 and 2). As the statin lipid-lowering agents, pravastatin and simvastatin known as HMG-CoA reductase inhibitors are known. As the fibrate lipid-lowering agents, fenofibrate and bezafibrate are known. It is thought that this reduction in HDL-cholesterol is due to functional inhibition of ABCA1 (for example, refer to Non-Patent Documents 3, 4, and 5).

It is known that probucol spiroquinone, probucol diphenoquinone, and probucol bisphenol according to the present invention are produced as metabolites when probucol is orally administered to a mammal (for example, prefer to Non-Patent Document 6).

Some pharmacological activities of probucol spiroquinone, probucol diphenoquinone, and probucol bisphenol (hereinafter sometimes preferred to as "bisphenol-type compounds", or collectively the "bisphenol-type compound") are known at present. For example, it is disclosed that probucol bisphenol has antioxidant properties and is used in combination with probucol as a lipoprotein oxidation inhibitor (for example, refer to Patent Document 1). In addition, it is known that the bisphenol-type compounds incorporate cholesterol into cells (for example, refer to Non-Patent Document 7). However, in these prior findings, functions of the bisphenol-type compounds on ABCA1 and HDL are not disclosed at all.

HDL is a lipid/protein complex particle produced by the action of helix-like apolipoproteins such as apoprotein A-I (hereinafter sometimes referred to as "apoAI") mainly synthesized in and secreted from liver cells and small-intestine epithelial cells and the ABCA1 protein present in cell membranes. Immediately after secretion, HDL is formed as a discoidal particle composed of major constituents, apoAI and phospholipid, and called nascent HDL. This nascent HDL receives, in blood, free cholesterol from cell membranes of peripheral cells or surfaces of other lipoproteins, and forms mature spherical HDL while holding, at its hydrophobic center, cholesterol ester converted from the cholesterol by the action of LCAT (lecithin cholesterol acyltransferase).

In the above-mentioned process, HDL plays a major role in extremely important physiological function in terms of lipid metabolism called "cholesterol reverse-transport system" which takes, in blood, excessive cholesterol out of peripheral tissues and transports it to the liver. The cholesterol reverse-transport system is considered to work for removing cholesterol accumulated in blood vessel wall cells and to cause a prophylactic action on arteriosclerosis.

With respect to a relationship between blood levels of HDL cholesterol and arteriosclerosis, many epidemiological studies have been conducted. As a result, it has been recently revealed a fact that lower HDL cholesterol levels result in a higher incidence of arteriosclerosis. The improvement of low HDL-cholesterolemia is a more important and novel technology as prophylactic/therapeutic treatment of arteriosclerosis, compared to a therapy using the statins or fibrates widely used at present for reducing LDL.

At present, the blood level of HDL is determined by referring to the level of HDL-cholesterol. In general, when the blood HDL cholesterol level of a subject is lower than 40 mg/dl, the subject is diagnosed as "low-HDL cholesterolemia".

Low-HDL cholesterolemia is found as a risk factor at a high incidence in not only arteriosclerosis but also in various disorders such as hyperlipidemia, myocardial infarction, cerebral infarction, cerebral apoplexy, obesity, diabetes mellitus, and nerve disorders caused by diabetes mellitus. Low-HDL cholesterolemia is also caused by various genetic diseases including Tangier disease. However, a useful prophylactic/therapeutic agent that acts on HDL itself has been desired to be developed. Such a prophylactic/therapeutic agent for treatment of low-HDL cholesterolemia has not been found yet.

In order to treat low-HDL cholesterolemia, a number of trials for increasing HDL have been conducted. As a result of such trials, pharmacological effects of ABCA1 have been identified.

ABCA1 is a protein mainly present in cell membranes of various organs such as the liver, small intestine, placenta, and adrenal gland, and belongs to the ABC protein family that is considered to be involved in membrane transport of various substances such as lipids, amino acids, vitamins, and saccharides (for example, refer to Non-Patent Document 8).

A recent finding revealed that ABCA1 was a protein indispensable for a reaction generating HDL from lipids in cells and a rate-limiting factor of HDL production. In addition, it was revealed that the HDL formation by ABCA1 is a main removing pathway of cellular cholesterol.

For example, in patients with Tangier disease whose ABCA1 gene has a mutation and who are deficient in expressing ABCA1, plasma HDL almost disappears (for example, refer to Non-Patent Documents 9, 10, and 11). In addition, it was found that incorporation of ABCA1 gene accelerates a HDL-generating reaction (for example, referred to Non-Patent Documents 12 and 13). Several trials are now in progress to elevate or regulate HDL cholesterol levels by increasing the ABCA1 expression level in vivo with genetic engineering technology.

For example, for increasing cholesterol efflux and HDL levels, the expression level and activity of ABCA1 are elevated by direct gene transfer of an ABCA1-coding gene into a host cell (for example, refer to Patent Documents 2 and 3). The expression and activity of ABCA1 are increased by using a certain substance to facilitate the transcription and translation of the ABCA1 gene for controlling the levels of HDL cholesterol and triglyceride (for example, refer to Patent Document 4). Furthermore, for controlling the cholesterol efflux to the outside of cells, the expression of ABCA1 is increased by activating peroxisome proliferator activated receptor-α (PPAR-α) or peroxisome proliferator activated receptor-δ (PPAR-δ) having various activities as an intranuclear receptor (for example, refer to Patent Document 5).

However, in the above-mentioned known technologies focused on ABCA1 and HDL, a genetic engineering technology or a method for activating an intranuclear receptor is used. Therefore, there are disadvantages such that the technology for a genetic therapy is immature and that a risk of unexpected side effects caused by activating an unknown gene is not ignorable. Thus, the use as a drug has not been accomplished yet.

[Patent Document 1] International Publication WO 02/04031
[Patent Document 2] International Publication WO 00/78971
[Patent Document 3] International Publication WO 00/78972
[Patent Document 4] International Publication WO 01/15676
[Patent Document 5] Japanese Unexamined Patent Application Publication No. 2003-12551
[Non-Patent Document 1] CIRCULATION, (US), 79, 1989, 16-28
[Non-Patent Document 2] JOURNAL of CARDIOVASCULAR PHARMACOLOGY, (US), 30, 1997, 784-789
[Non-Patent Document 3] BIOCHEMISTRY, (US), 35(40), 1996, 13011-13020
[Non-Patent Document 4] BIOCHIMICA et BIOPHYSICA ACTA, (Netherlands), 1483, 2000, 199-213
[Non-Patent Document 5] Arteriosclerosis, thrombosis, and vascular biology, (US), 21, 2001, 394-400
[Non-Patent Document 6] ANALYTICAL CHEMISTRY SYMPOSIA SERIES, (US), 7, 1981, 35-38
[Non-Patent Document 7] LIPIDS, (US), 29(12), 1994, 819-823
[Non-Patent Document 8] ANNUAL REVIEW of CELL BIOLOGY, (US), 8, 1992, 67-113
[Non-Patent Document 9] NATURE GENETICS, (US), 22, 1999, 336-345
[Non-Patent Document 10] NATURE GENETICS, (US), 22, 1999, 347-351
[Non-Patent Document 11] NATURE GENETICS, (US), 22, 1999, 352-355
[Non-Patent Document 12] THE JOURNAL of CLINICAL INVESTIGATION, (US), 104, 1999, R25-R31
[Non-Patent Document 13] THE FASEB JOURNAL, (US), 15, 2001, 1555-1561

SUMMARY OF THE INVENTION

As described above, low-HDL cholesterolemia is often observed in hyperlipidemia, obesity, and diabetes mellitus and is a serious risk factor of arterioscleroses such as myocardial infarction, cerebral infarction, and cerebral apoplexy. The present invention provides a prophylactic/therapeutic agent for various diseases such as arteriosclerosis based on mechanisms wherein ABCA1 is stabilized with a specific bisphenol-type compound, thereby resulting in elevating ABCA1 levels followed by an increase in production of HDL.

The present inventors have studied for various materials in order to overcome the above-mentioned disadvantages in the conventional method and to find an agent affecting an HDL-generating mechanism and being useful as a prophylactic/therapeutic agent for low-HDL cholesterolemia. As a result, the inventors have found a prophylactic/therapeutic agent for low-HDL cholesterolemia and filed a patent application already published as WO 03/033023 A1. The agent contains an effective amount of a cysteine-protease inhibitor which suppresses or inhibits the degradation of ABCA1, thereby resulting in elevated ABCA1 levels.

The present inventors have further conducted extensive studies and succeeded in finding that the aforementioned bisphenol-type compounds have actions of suppressing or inhibiting the degradation of ABCA1 to cause the continuous and stable expression of ABCA1, thereby leading to elevated HDL levels. Thus, the present invention has been provided. The HDL level-elevating action of the bisphenol-type compounds is quite contrary to the function of probucol which has been hitherto known to decrease the HDL level relying on inhibition of the ABCA1 function. Hence, the present invention is not predictable at all from the above-mentioned known technologies. Thus, the present invention provides an agent which overcomes the defect of probucol.

The present invention provides an ABCA1 stabilizer comprising an effective amount of a bisphenol-type compound selected from probucol spiroquinone, probucol diphenoquinone, probucol bisphenol, and salts thereof (hereinafter sometimes simply preferred to as "the bisphenol-type compounds" or "said bisphenol-type compounds"); a prophylactic/therapeutic agent for low-HDL cholesterolemia, which comprises an effective amount of said ABCA1 stabilizer; a prophylactic/therapeutic agent for arteriosclerosis, which comprises an effective amount of said ABCA1 stabilizer; and a drug comprising an effective amount of at least one member selected from the group consisting of said ABCA1 stabilizer, said prophylactic/therapeutic agent for low-HDL cholesterolemia, and said prophylactic/therapeutic agent for arteriosclerosis, in combination with an effective amount of at least one drug selected from the group consisting of antidiabetes drugs, therapeutic drugs for complications of diabetes, antiobesity drugs, antihypertensive drugs, antihyperlipidemic drugs, diuretics, antithrombotic drugs, and anti-Alzheimer drugs.

The present invention further provides an agent for 1) elevating the in vivo level of ABCA1 and accelerating in vivo HDL-generating reaction, 2) elevating the blood level of HDL, 3) increasing the activity of the blood cholesterol reverse transport that removes cholesterol from peripheral tissues, and/or 4) suppressing or inhibiting the degradation of ABCA1 and accelerating the HDL-generating reaction in vivo, which comprises an effective amount of said bisphenol-type compounds. The present invention further provides a prophylactic/therapeutic agent for low-HDL cholesterolemia, which comprises an effective amount of said agent according to any of the above 1) to 4); a prophylactic/therapeutic agent for arteriosclerosis, which comprises an effective amount of said agent according to any of the above 1) to 4); and a drug comprising an effective amount of at least one agent according to any of the above 1) to 4), in combination with an effective amount of at least one drug selected from the group consisting of antidiabetes drugs, therapeutic drugs for complications of diabetes, antiobesity drugs, antihypertensive drugs, antihyperlipidemic drugs, diuretics, antithrombotic drugs, and anti-Alzheimer drugs.

The present invention further provides A) a method for a) stabilizing ABCA1, b) increasing the ABCA1 level and accelerating the HDL-generating reaction in vivo, c) increasing the blood level of HDL, d) increasing activity of the blood cholesterol reverse-transport system which removes cholesterol from peripheral tissues, and/or e) suppressing the degradation of ABCA1 and accelerating the HDL-generating reaction in vivo, which comprises administering an effective dose of the bisphenol-type compounds to a subject (or patient). The present invention further provides B) a method for prophylactic/therapeutic treatment of low-HDL cholesterolemia which comprises administering an effective dose of any one of the above-mentioned agents to a subject; C) a method for prophylactic/therapeutic treatment of arteriosclerosis, which comprises administering an effective dose of any one of the above-mentioned agents to a subject (or patient); and D) a method for prophylactic/therapeutic treatment of a disease, which comprises administering an effective dose of any one of the above-mentioned agents, in combination with an effective dose of at least one drug selected from the group consisting of antidiabetes drugs, therapeutic drugs for complications of diabetes, antiobesity drugs, antihypertensive drugs, antihyperlipidemic drugs, diuretics, antithrombotic drugs, and anti-Alzheimer drugs.

ADVANTAGEOUS PROFILES OF THE INVENTION

The ABCA1 stabilizer according to the present invention, which contains, as an effective ingredient, a bisphenol-type compound selected from probucol spiroquinone, probucol diphenoquinone, probucol bisphenol, and salts thereof, facilitates, free of requiring genetic engineering techniques, continuous and stable ABCA1 expression with a mechanism completely different from the conventional technologies. The ABCA1 stabilizer exerts the efficacy of ameliorating various diseases, such as low-HDL cholesterolemia, which arise due to a decrease in the ABCA1 expression. In addition, since the stabilizer utilizes a metabolite of probucol which has been used as a drug, it is advantageous as a highly safe pharmaceutical drug. The present invention further provides an agent for increasing the ABCA1 level and accelerating the HDL-generating reaction in vivo, increasing the blood level of HDL, enhancing the activity of blood cholesterol reverse-transport system which takes up cholesterol from peripheral tissues, and/or suppressing the degradation of ABCA1 and accelerating the HDL-generating reaction in vivo, which contains at least one of the bisphenol compounds as an effective ingredient. The present invention further provides a method for prophylactic/therapeutic treatment of various diseases or abnormal conditions (specifically, being associated with a decrease in the HDL blood level) which comprises administering at least one of the bisphenol-type compounds.

The above objects and other objects, features, advantages, and aspects of the present invention are readily apparent to those skilled in the art from the following disclosures. It should be understood, however, that the description of the specification including the following best modes of carrying out the invention, specific examples, etc. is illustrating preferred embodiments of the present invention and given only for illustrative purposes. It will become apparent to the skilled in the art that a great number of variations and/or alterations (or modifications) of this invention may be made based on knowledge from the disclosure in the following parts and other parts of the specification without departing from the spirit and scope thereof as disclosed herein. All of the patent publications and reference documents cited herein for illustrative purposes are hereby incorporated by reference into the present disclosure.

BEST MODES OF CARRYING OUT THE INVENTION

The present invention provides:

1) an ABCA1 stabilizer comprising an effective amount of at least one bisphenol-type compound selected from probucol spiroquinone, probucol diphenoquinone, probucol bisphenol, and salts thereof;

2) a prophylactic/therapeutic agent for low-HDL cholesterolemia which comprises at least one ABCA1 stabilizer according to the above 1);

3) a prophylactic/therapeutic agent for arteriosclerosis which comprises at least one ABCA1 stabilizer according to the above 1); and 4) a drug comprising at least one member selected from the group consisting of ABCA1 stabilizers, prophylactic/therapeutic agents for low-HDL cholesterolemia, and prophylactic/therapeutic agents for arteriosclerosis, according to any of the above 1) to 3), in combination with at least one drug selected from the group consisting of antidiabetes drugs, therapeutic drugs for complications of diabetes, antiobesity drugs, antihypertensive drugs, antihyperlipidemic drugs, diuretics, antithrombotic drugs, and anti-Alzheimer drugs.

The present invention further provides:

5) an agent for increasing the in vivo level of ABCA1 and accelerating the in vivo HDL-generating reaction which comprises an effective amount of at least one bisphenol-type compound selected from probucol spiroquinone, probucol diphenoquinone, probucol bisphenol, and salts thereof;

6) an agent for increasing the blood level of HDL which comprises an effective amount of said bisphenol compound;

7) an agent for increasing the activity of cholesterol reverse-transport that takes up, in blood, cholesterol from peripheral tissues, which comprises an effective amount of said bisphenol-type compounds;

8) an agent for suppressing or inhibiting the in vivo degradation of ABCA1 and accelerating the in vivo HDL-generating reaction which comprises an effective amount of said bisphenol-type compounds;

9) a prophylactic/therapeutic agent for low-HDL cholesterolemia which comprises an effective amount of at least one member selected from agents according to the above 5) to 8);

10) a prophylactic/therapeutic agent for arteriosclerosis which comprises an effective amount of at least one member selected from agents according to the above 5) to 8); and 11) a drug comprising an effective amount of at least one member selected from agents according to the above 5) to 10), in combination with at least one drug selected from the group consisting of antidiabetes drugs, therapeutic drugs for complications of diabetes, antiobesity drugs, antihypertensive drugs, antihyperlipidemic drugs, diuretics, antithrombotic drugs, and anti-Alzheimer drugs.

The present invention further provides:

a) a method for stabilizing ABCA1 which comprises administering an effective dose of at least one bisphenol-type compound selected from probucol spiroquinone, probucol diphenoquinone, probucol bisphenol, and salts thereof to a subject;

b) a method for increasing the in vivo level of ABCA1 and accelerating HDL-generation in vivo which comprises administering an effective dose of said bisphenol-type compounds to a subject;

c) a method for increasing the blood level of HDL which comprises administering an effective dose of said bisphenol-type compounds to a subject;

d) a method for increasing the activity of cholesterol reverse-transport that takes up, in blood, cholesterol from peripheral tissues, which comprises administering an effective dose of said bisphenol-type compounds to a subject;

e) a method for suppressing or inhibiting the degradation of ABCA1 and accelerating in vivo HDL-generation which comprises administering an effective dose of said bisphenol-type compounds to a subject;

f) a method for prophylactic/therapeutic treatment of low-HDL cholesterolemia which comprises administering an effective dose of at least one agent according to any of the above 1) and 5) to 8) to a subject;

g) a method for prophylactic/therapeutic treatment of arteriosclerosis which comprises administering an effective dose of at least one agent according to any of the above 1) and 5) to 8) to a subject; and h) a method for prophylactic/therapeutic treatment of a disease which comprises administering an effective dose of at least one agent according to any of the above 1) to 3) and 5) to 10), in combination with an effective dose of at least one drug selected from the group consisting of antidiabetes drugs, therapeutic drugs for complications of diabetes, antiobesity drugs, antihypertensive drugs, antihyperlipidemic drugs, diuretics, antithrombotic drugs, and anti-Alzheimer drugs.

The present invention provides A) a pharmaceutical drug containing, as an effective component, a bisphenol-type compound selected from probucol spiroquinone, probucol diphenoquinone, probucol bisphenol, and salts thereof; and B) a pharmaceutical composition containing a pharmaceutically effective dose of a bisphenol-type compound selected from probucol spiroquinone, probucol diphenoquinone, probucol bisphenol, and salts thereof, in admixture with a pharmaceutically acceptable excipient.

The above-mentioned probucol spiroquinone, probucol diphenoquinone, and probucol bisphenol can be chemically synthesized by techniques, for example, disclosed in the Examples herein below. These compounds can be also isolated and purified by biochemical techniques and chemical techniques, which are generally used, from in vivo metabolites produced when probucol is administered to a mammal.

Among the aforementioned bisphenol-type compounds, when they are capable of forming salts, preferable salts thereof encompass pharmaceutically acceptable salts, including, for example, salts with inorganic or organic bases; salts with neutral, basic, or acidic amino acids; etc. Preferable examples of the inorganic bases include alkaline metals such as sodium and potassium; alkali earth metals such as calcium and magnesium; aluminum; ammonium; etc. Preferable examples of the organic bases include trimethylamine, triethylamine, pyridine, picoline, ethanolamine, diethanolamine, triethanolamine, dicyclohexylamine, N,N-dibenzylethylenediamine, etc. Preferable examples of the neutral amino acids include glycine, valine, leucine, etc. Preferable examples of the basic amino acids include arginine, lysine, ornithine, etc. Preferable examples of the acidic amino acids include aspartic acid, glutamic acid, etc.

The ABCA1 stabilizer is an agent or drug that provides the continuous and stable expression of ABCA1 mainly present in cell membranes of various organs such as liver, small intestine, placenta, and adrenal gland. The stabilization of ABCA1 may refer to a state in which ABCA1 is being continuously and stably expressed. Examples of such a state may include, when ABCA1 levels are compared between in the presence and absence of the ABCA1 stabilizer, a state in which ABCA1 is more continuously and stably present in cells (in particular, in cell membranes), a state in which ABCA1 is present in cells (in particular, in cell membranes) so as to further accelerate the HDL-generating reaction, and a state in which ABCA1 is present in cells (in particular, in cell membranes) so as to further suppress or inhibit the degradation of ABCA1, under the effect of the ABCA1 stabilizer.

The prophylactic/therapeutic agent for low-HDL cholesterolemia is a drug that prevents, relieves or cures low-HDL cholesterolemia. Low-HDL cholesterolemia is observed in diseases such as, in particular, arteriosclerosis, hyperlipidemia, myocardial infarction, cerebral infarction, cerebral apoplexy, obesity, diabetes mellitus, nerve disorders caused by diabetes mellitus, thyroid dysfunction, hepatocirrhosis, myeloma, chronic renal failure, and chronic inflammatory bowel disease (examples: Crohn's disease, chronic ulcerative colitis). The prophylactic/therapeutic agent for low-HDL cholesterolemia comprising the ABCA1 stabilizer according to the present invention can be used for prophylactic/therapeutic treatment of any of the above-mentioned diseases excepting genetic diseases, such as Tangier disease, in which ABCA1 is not normally synthesized in vivo.

The prophylactic/therapeutic agent for arteriosclerosis is a drug that prevents, relieves or cures arteriosclerosis. The ABCA1 stabilizer according to the present invention potently act in accelerating HDL-generation to increase blood HDL levels (or increase plasma HDL levels or serum HDL levels) as it will be clear from Assay Examples herein below. The blood HDL plays an important role in the cholesterol reverse-transport system which prophylactically acts on arteriosclerosis. The drug of the present invention is also useful as a prophylactic/therapeutic agent for arteriosclerosis via the action of increasing the blood HDL level.

In other words, in low-HDL cholesterolemia, the cholesterol reverse-transport system cannot sufficiently work due to a decrease in the HDL level. Consequently, cholesterol accumulated in vascular walls is not readily transferred to the outside of the blood vessel, thereby resulting in acceleration of arteriosclerosis. Such a condition can be ameliorated with the prophylactic/therapeutic agent for low-HDL cholesterolemia according to the present invention. Thus, the agent can be prophylactically and therapeutically applied to arteriosclerosis. Similarly, the bisphenol-type compounds are useful for increasing the ABCA1 level and accelerating the HDL-generating reaction in vivo; increasing the blood level of HDL; increasing the cholesterol reverse-transport system activity in blood, which takes up cholesterol from peripheral tissues; and/or suppressing or inhibiting the degradation of ABCA1 and accelerating the HDL-generating reaction in vivo. Therefore, the bisphenol compound can be used for prophylactic/therapeutic treatment of low-HDL cholesterolemia and arteriosclerosis.

In addition, the ABCA1 stabilizer of the present invention is useful for various diseases which are thought to be caused by a decrease in the ABCA1 expression, as follows:

Coronary artery disease (including cardiac infarction, angina pectoris, asymptomatic myocardial ischemia, and coronary arteriosclerosis); atherosclerosis; carotid arteriosclerosis; cerebrovascular disease (including cerebral apoplexy and cerebral infarction); arteriosclerosis obliterans; fatty liver; hepatocirrhosis; myeloma; diabetes mellitus; diabetic complication; dermatologic disease; xanthomatosis; arthritic disorder; proliferative disease; peripheral arterial obstruction; ischemic peripheral circulatory failure; obesity; cerebrotendinous xanthomatosis (CTX); chronic renal failure; glomerular nephritis; arteriosclerotic nephritis; vascular thickening; vascular thickening after intervention (including percutaneous coronary plasty, percutaneous coronary revascularization, detention of stent, coronary endoscopy, intravascular sonication, and percutaneous transluminal thrombolytic therapy); vascular reocclusion and restenosis after bypass operation; nephropathy, nephritis, and pancreatitis, which highly relate to hyperlipidemia; hyperlipidemia (including familial hypercholesterolemia and postprandial hyperlipidemia); chronic inflammatory bowel disease (including Crohn's disease and chronic ulcerative colitis); intermittent claudication; deep venous thrombosis; malaria encephalitis; Alzheimer's disease; and diseases accompanied with wound or ateliosis.

The drug containing the active ingredient according to the present invention is effective for prophylactic/therapeutic treatment of various diseases or abnormal conditions which are associated with a decrease in the blood HDL level, and is obviously useful for the above-mentioned diseases.

The ABCA1 stabilizer, prophylactic/therapeutic agent for low-HDL cholesterolemia, and prophylactic/therapeutic agent for arteriosclerosis according to the present invention may be administered alone or in combination with other drugs described below, preferably in a form of a drug containing a pharmaceutically acceptable excipient. The agent is administered by an oral route or injection. In addition, the drug may be in topical form (such as percutaneous drug or ointment), suppository form (such as rectal suppository and vaginal suppository), pellet form, nasal-drop form, inhalant form (such as a form using a nebulizer), or eye-drops form. In any administration route of the drug, a component (hereinafter sometimes referred to as "pharmaceutical component") selected from known pharmaceutical excipients can be optionally used. Specifically, examples of known excipients are disclosed in, for example, (1) Iyakuhin Tenkabutsu Handobukku (Handbook of Pharmaceutical Excipients), MARUZEN, 1989, (2) Iyakuhin Tenkabutu Jiten (Encyclopedia of Pharmaceutical Excipients), 1st Edition, Yakuji Nippo, 1994, (3) Iyakuhin Tenkabutsu Jiten Tsuiho (Encyclopedia of Pharmaceutical Excipients, Supplement), 1st Edition, Yakuji Nippo, 1995, and (4) Yakuzaigaku (Pharmacology), Revised 5th Edition, Nankodo, 1997. The pharmaceutical component may be optionally selected from the known pharmaceutical excipients shown above depending on the administration route and application purpose of the drug. Similarly, the agent of the present invention for increasing the ABCA1 level and accelerating the HDL-generating reaction in vivo; increasing the blood level of HDL; increasing activity of the cholesterol reverse-transport system in blood, which removes cholesterol from peripheral tissues; and/or suppressing the degradation of ABCA1 and accelerating the HDL-generating reaction in vivo may be administered as described above.

For example, when the drug is administered orally, any excipient can be used as long as the excipient can constitute an oral drug as a pharmaceutical component and achieve purposes of the present invention. Generally, the excipient is selected from known pharmaceutical components including for example fillers, binders, disintegrants, lubricants, and coating agents (including taste masking agents). Examples of the oral drug include tablets (including sublingual tablets and orally disintegrating tablets), capsules (including soft capsules and microcapsules), granules, fine granules, powders, troches, and syrups. The oral drugs include those (examples: rapid-release drugs and sustained-release drugs) in which a known pharmaceutical component is used to control the in vivo release of an active component (i.e., an effective ingredient), i.e., the in vivo release of probucol spiroquinone, probucol diphenoquinone, or probucol bisphenol.

When the drugs are administered by injection routes, the excipient used includes any pharmaceutical component which can constitute an aqueous injection or non-aqueous injection. In general, known pharmaceutical components which are used include dissolving agents, dissolving aids, suspending agents, isotonizing agents, buffering agents, stabilizing agents, preservatives, etc. In addition, the excipient used may include known pharmaceutical compounds which constitute powder injections. The powder injections are used after being dissolved or suspended when they are administered. Examples of the pharmaceutical components for aqueous injections include distilled water for injection and sterile isotonic salt solutions (containing, for example, monosodium phosphate, disodium phosphate, sodium chloride, potassium chloride, calcium chloride, magnesium chloride, or a mixture thereof) Examples of the pharmaceutical components for non-aqueous injections include vegetable oils such as olive oil, sesame oil, cotton oil, and corn oil; propylene glycol; macrogol; and tricapryline. The drugs are prepared by dissolving, suspending, or emulsifying the active component in these pharmaceutical components. Examples of the injections include subcutaneous injections, intravenous injections, intramuscular injections, intraperitoneal injections, and intravenous drips. Provided thus is use of the bisphenol-type compounds for preparing drugs (pharmaceutical drugs or pharmaceutical compositions) which contain the active ingredient or active component of the present invention and have the above-mentioned activities.

The effective dose of the ABCA1 stabilizer, prophylactic/therapeutic agent for low-HDL cholesterolemia, and prophylactic/therapeutic agent for arteriosclerosis according to the present invention varies and is optionally controlled depending on the age and weight of a subject, symptoms of the low-HDL cholesterolemia or arteriosclerosis, and the presence or absence of complications. In general, the dose is about 0.1 to 3000 mg/day when the agent is administered orally, and the dose is about 0.1 to 1000 mg/day when the agent is administered by injection. Similarly, the agent of the present invention for increasing the ABCA1 level and accelerating the in vivo HDL-generating reaction; increasing the blood level of HDL; activating or stimulating the cholesterol reverse transport pathway in blood, which removes cholesterol from peripheral tissues; and/or suppressing the degradation of ABCA1 and accelerating the in vivo HDL-formation may be administered as described above.

The ABCA1 stabilizer, prophylactic/therapeutic agent for low-HDL cholesterolemia, and prophylactic/therapeutic agent for arteriosclerosis according to the present invention can be used as a combination with one or more other drugs, which do not adversely affect actions of the inventive agents, in order to increase the efficacy, reduce the dose to be administered, and decrease side-effects. The drug used in the combination may include low molecular-weight compounds, polypeptides, antibodies, vaccines, etc. Such drugs include, for example, "antidiabetes drugs", "therapeutic drugs for complications of diabetes", "antiobesity drugs", "antihypertensive drugs", "antihyperlipidemic drugs", "diuretics", "antithrombotic drugs", "anti-Alzheimer drugs", and others. Similarly, the agent of the present invention for elevating the ABCA1 level and accelerating the HDL formation in vivo; increasing the blood level of HDL; activating the cholesterol reverse-transport pathway in blood, which removes cholesterol from peripheral tissues; and/or inhibiting the degradation of ABCA1 and accelerating the HDL formation in vivo may be administered as described above.

The "antidiabetes drug" includes, for example, insulin secretagogues, biguanides, insulin, and α-glucosidase inhibitors. The insulin secretagogue includes, for example, tolbutamide, chlorbutamide, chlorpropamide, tolazamide, acetohexamide, glyclopyramide, glibenclamide, gliclazide, glibuzol, glimepirid, nateglinide, and mitiglinide. The biguanide includes, for example, phenformin, metformin, and buformin. The α-glucosidase inhibitor includes, for example, acarbose, voglibose, miglitol, and emiglitol.

The "therapeutic drug for complications of diabetes" includes, for example, aldose-reductase inhibitors such as epalrestat, alprostadil, and mexiletine hydrochloride.

The "antiobesity drug" includes, for example, lipase inhibitors and appetite suppressants. The lipase inhibitor includes, for example, orlistat. The appetite suppressant includes, for example, dexfenfluramine, fluoxetine, sibutramine, and baiamine.

The "antihypertensive drug" includes, for example, angiotensin-converting enzyme inhibitors, calcium antagonists, and angiotensin II antagonists. The angiotensin-converting enzyme inhibitor includes, for example, captopril, enalapril, alacepril, delapril, lisinopril, imidapril, benazepril, cilazapril, perindopril, quinapril, temocapril, trandolapril, and manidipine. The calcium antagonist includes, for example, nifedipine, amlodipine, efonidipine, and nicardipine. The anigotensin II antagonist includes, for example, losarutan, cardesartan cilexetil, valsartan, and irbesartan.

The "antihyperlipidemic drug" includes, for example, HMG-CoA reductase inhibitors and fibrates. The HMG-CoA reductase inhibitor includes, for example, statins such as pravastatin, simvastatin, lovastatin, atorvastatin, and fluvastatin. The fibrates include, for example, bezafibrate, clinofibrate, clofibrate, fenofibrate, and simfibrate. In addition to the above-mentioned drugs, the "antihyperlipidemic drug" includes, for example, anion exchange resins (example: cholestyramine), nicotinic acid agents (examples: nicomol and niceritrol), and ethyl icosapentate.

The "diuretic" includes, for example, thiazide drugs such as cyclopenthiazide, trichloromethiazide, hydrochlorothiazide, hydroflumethiazide, benzylhydrochlorothiazide, penfluthizide, and methyclothiazide. In addition to the above-mentioned drugs, the diuretic includes isosorbide and furosemide.

The "antithrombotic drug" includes, for example, heparin, warfarin, antithrombin agents, thrombolytic agents, and platelet-aggregation-suppressing agents (anti-platelet agents).

The "anti-Alzheimer drug" includes, for example, donepezil, rivastigmine, and galantamine.

When the ABCA1 stabilizer, prophylactic/therapeutic agent for low-HDL cholesterolemia, or prophylactic/therapeutic agent for arteriosclerosis according to the present invention is applied in combination with any of the concomitant agents, the dosage form is not specifically limited as long as the agent of the present invention is coadministered with the concomitant agent. Examples of such dosage forms include those for administrating a single dosage unit prepared by formulating the agent of the present invention and the concomitant agent together; for administrating two kinds of drugs at the same time or at an interval via identical routes, wherein the two kinds of drugs are prepared by separately formulating the agent of the present invention and the concomitant agent; and for administrating two kinds of drugs at the same time or at an interval via different routes, wherein the two kinds of drugs are prepared by separately formulating the agent of the present invention and the concomitant agent.

The present invention provides a method for prophylactic/therapeutic treatment of diseases with the bisphenol-type compounds. For example, the method for prophylactic/therapeutic treatment of diseases can be performed by administering an effective dose of the bisphenol-type compounds to a subject or target. The inventive method for prophylactic/therapeutic treatment of diseases may be performed while monitoring conditions and symptoms of a subject. The monitoring may be conducted at regular or irregular intervals of time, or may be periodically conducted. Typically, the method is performed while monitoring the blood HDL level. The drugs of the present invention may be administered at regular or irregular intervals of time, or may be periodically administered.

The term "prophylactic/therapeutic treatment" used herein refers to preventive treatment and/or curative treatment, i.e., including (1) prophylactic and therapeutic treatments, and (2) prophylactic treatment or therapeutic treatment.

EXAMPLES, ETC.

Details of the present invention are described by the following examples including Synthesis Examples, Assay Examples, and Formulation Examples, but such examples are provided only for illustrative purposes, and for referential embodiments of the present invention. These examples should in no way be construed as limiting and restricting the scope of the invention disclosed herein. It should be understood in the present invention that various embodiments can be made or executed within the spirit, scope and concept disclosed herein.

All the Assay Examples and other Examples were performed or can be performed, unless otherwise disclosed herein specifically, according to standardized techniques which are well-known and conventional to those skilled in the art. In Examples herein below, specific processes and treatment conditions were performed, unless specific indication is provided, according to attached protocols with attached reagents when commercially available reagents or kits were used.

Synthesis Example 1

Synthesis of Probucol Spiroquinone

A mixture of probucol (981 mg, 1.9 mmol: Wako Pure Chemical Industries, Ltd.) and lead oxide (4.04 g) in dichloromethane (20 mL) was stirred overnight. The mixture was filtered, evaporated, then washed with methanol, and dried to yield a crystal, probucol spiroquinone (912 mg, 93%). Chemical ionization mass spectra (CI-MS) were recorded on a double-focusing magnetic sector mass spectrometer (MS700: JEOL). Elemental analysis was conducted with a CHN autoanalyzer (Vario EL: Elementar).

mp 156-158° C. $^1$H NMR (CDCl$_3$) δ: 1.20 (36H, s), 2.01 (6H, s), 6.88 (4H, s) CI(positive)-MS (m/z): 515 (M+1), 473 (M-C$_3$H$_6$), 441 (M-C$_3$H$_6$S+1), 409 (M-C$_3$H$_6$S$_2$+1, diphenoquinone+1), 279 (M-C$_{14}$H$_{20}$OS+1), 237 (C$_{14}$H$_{20}$OS+1) Anal. calcd. for C$_{31}$H$_{46}$O$_2$S$_2$: C, 72.32; H, 9.01. Found: C, 72.3; H, 9.0.

Synthesis Example 2

Synthesis of Probucol Diphenoquinone

A methanol solution (100 mL) of 2,6-di-t-butylphenol (309 mg, 1.5 mmol) was oxidized under the presence of phthalocyanine-Fe (II) (853 mg, 1.5 mmol) at a room temperature for 5 hours according to a method of Tada, et al. [Bull. Chem. Soc., 45, 2558-2559, (1972)]. The resultant reaction mixture was stirred until the reaction was completed, and then evaporated. The resulting residue was dissolved in ethanol, filtered, and evaporated to yield a crystal, probucol diphenoquinone (340 mg, 100%). Electron impact mass spectra (EI-MS) were recorded on a double-focusing mass spectrometer (AX505W: JEOL).

mp 223-225° C. $^1$H NMR (CDCl$_3$) δ: 1.37 (36H, s), 7.71 (4H, s) EI-MS (m/z): 408 (M), 393 (M-CH$_3$), 351 (M-C$_4$H$_9$)

Synthesis Example 3

Synthesis of Probucol Bisphenol

To a solution of probucol diphenoquinone (349 mg, 0.86 mmol), prepared in Synthesis Example 2, in methanol (20 mL) and dichloromethane (20 mL) was added sodium borohydride (72 mg, 1.88 mmol) under nitrogen atmosphere. The resultant reaction mixture was stirred for 1 hour, evaporated, then washed with water, and dried to yield a crystal, probucol bisphenol (244 mg, 70%). Electron impact mass spectra (EI-MS) were recorded on a double-focusing mass spectrometer (AX505W: JEOL).

mp 184-186° C. $^1$H NMR (CDCl$_3$) δ: 1.49 (36H, s), 5.18 (2H, s), 7.30 (4H, s) EI-MS (m/z): 410 (M), 395 (M-CH$_3$)

Assay Example 1

Increase in the ABCA1 Expression by Probucol Spiroquinone, Probucol Diphenoquinone, and Probucol Bisphenol in THP-1 Cells <Assay Method>

THP-1 cells (human leukemia cells: American Type Culture Collection) were cultured for 72 hours in a 10% FBS-RPMI1640 medium (Iwaki Glass Co., Ltd.) under the presence of PMA (phorbol myristate acetate, $3.2 \times 10^{-7}$ M: Wako Pure Chemical Industries, Ltd.) to obtain differentiated macrophages. Probucol spiroquinone (Synthesis Example 1), probucol diphenoquinone (Synthesis Example 2), or probucol bisphenol (Synthesis Example 3) was added to a medium after being incorporated into acetyl-LDL according to a method of Tsujita, et al. [BIOCHEMISTRY, 35, 13011-13020 (1996)]. The cells were cultured in this medium for 48 hours, and then further cultured for 24 hours in the presence or absence of apoAI. The expression levels of intracellular ABCA1 were assayed according to a method disclosed herein below.

The agent-treated cells and non-treated cells were hypotonically disrupted in 5 mM Tris-HCl (pH 8.5), and then centrifuged (650 g for 5 minutes) to precipitate nuclear fractions. The supernatant was centrifuged at 105,000 g for 30 minutes to collect a total membrane fraction. The total membrane was dissolved in a solution containing 0.9 M urea, 0.2% Triton X-100, and 0.1% dithiothreitol, followed by addition of 10% lithium dodecyl sulfate solution at a volume ratio of 1/4. The resultant was subjected to electrophoretic separation using 10% SDS-7% polyacrylamide gel. The separated proteins were transferred and fixed onto PVDF membrane (Bio-Rad), and then subjected to immunoblotting with anti-human ABCA1 rabbit antibody (self-purified by an ordinary technique) to examine expressed ABCA1 protein levels. The obtained bands of the protein were read for density and size with Scion Image (image analysis software: Scion) to convert the results into digitized forms. The relative ratio of the ABCA1 expression level of the drug-treated cells to that of the non-treated cells was calculated to evaluate the ABCA1-expression activity of the assayed compounds. The results are shown in Table 1.

<Results>

As shown in Table 1, it was observed that the intracellular ABCA1 expression levels of the THP-1 cells treated with probucol spiroquinone, probucol diphenoquinone, or probucol bisphenol were remarkably elevated, as compared with that of the non-treated cells.

TABLE 1

| Assayed Compound | ABCA1 Expression Level (Relative Ratio %) |
|---|---|
| Control (Non-treated) | 100 |
| Probucol spiroquinone | 191 |
| Probucol diphenoquinone | 173 |
| Probucol bisphenol | 153 |

Assay Example 2

Acceleration of HDL-generating Reaction by Probucol Spiroquinone, Probucol Diphenoquinone, and Probucol Bisphenol <Assay Method>

The cultured cells obtained in the same manner as in Assay Example 1 were examined for cholesterol and phospholipid taken out into the medium by the apoAI-dependent HDL-generating reaction, according to a method of Arakawa, et al. [J. LIPID RES., 41, 1952-1962, (2000)]. The results of the drug-treated cells were compared with that of non-treated cells (control). The resulting data were converted into digitized forms as in Assay Example 1, and the relative ratios of the taken out level in the drug-treated cells to that in the non-treated cells were calculated to evaluate the HDL-generating reaction accelerated by the assayed compounds. The results are shown in Table 2. For comparison, the HDL-generating reaction accelerated by probucol (Wako Pure Chemical Industries, Ltd.) was examined in the same manner as aforementioned.

<Results>

As shown in Table 2, it was observed that the levels of apoAI-dependently taken out HDL cholesterol were about 1.3 to 1.6 times elevated in the THP-1 cells treated with probucol spiroquinone, probucol diphenoquinone, or probucol bisphenol, as compared with that of the non-treated cells. Similarly, the levels of apoAI-dependently taken out phospholipid were also about 1.4 to 2.0 times increased in the THP-1 cells treated with probucol spiroquinone, probucol diphenoquinone, or probucol bisphenol, as compared with that of the non-treated cells. On the other hand, in the THP-1 cells treated with probucol, no apoAI-dependently taken out HDL cholesterol was observed and the level of taken out phospholipid was decreased to less than ⅓, as compared with that of the non-treated cells.

TABLE 2

| Assayed Compound | Release of HDL Cholesterol (Relative Ratio %) | Release of Phospholipid (Relative Ratio %) |
|---|---|---|
| Control (Non-treated) | 100 | 100 |
| Probucol spiroquinone | 148 | 151 |
| Probucol diphenoquinone | 159 | 200 |
| Probucol bisphenol | 137 | 144 |
| Probucol | 0 | 34 |

Assay Example 3

Increase of Blood HDL Level by Probucol Spiroquinone and Probucol Diphenoquinone (Mouse)

<Assay Method>

Probucol spiroquinone (Synthesis Example 1: 50 mg/kg or 150 mg/kg) or probucol diphenoquinone (Synthesis Example 2: 50 mg/kg or 150 mg/kg) suspended in a 0.5% carboxymethylcellulose solution was orally administered to each group of 3 or 4 mice once a day for 7 days. To a control group, only the 0.5% carboxymethylcellulose solution was administered in the same manner. Animals were subjected to laparotomy under ether anesthesia at 3 hours after the last administration, and blood was collected in the presence of heparin sodium from the heart of each mouse. The blood was centrifuged at 2000 g for 10 minutes to separate plasma. The plasma was applied to electrophoresis using Paragon Electrophoresis System (Beckman Coulter, Inc.) to separate plasma lipoprotein, followed by lipid staining. The images on the gel after the lipid staining were examined to covert the plasma HDL level of each mouse into a digitized form for the evaluation.

<Results>

As shown in Table 3, it was observed that the plasma HDL levels in mice administered with test drugs were increased about 1.2 times for probucol spiroquinone and about 1.1 to 1.8 times for probucol diphenoquinone, respectively, compared with that in control group.

TABLE 3

| Assayed Compound | Plasma HDL Level (Relative Ratio %) | |
| --- | --- | --- |
|  | 50 mg/kg | 150 mg/kg |
| Control (Non-treated) | 100 | 100 |
| Probucol spiroquinone | 120 | 124 |
| Probucol diphenoquinone | 113 | 180 |

Assay Example 4

Increase of Blood HDL Level by Probucol Spiroquinone, Probucol Diphenoquinone, and Probucol Bisphenol (Rabbit)

<Assay Method>

Microemulsions were prepared by adding probucol spiroquinone (Synthesis Example 1), probucol diphenoquinone (Synthesis Example 2), or probucol bisphenol to a mixture of triolein (Sigma Chemical Co.) and phosphatidyl choline (Avanti Polar Lipids). The microemulsion (0.5 to 10 mL/body) was administered to each group of 4 rabbits via the ear vein once a day for 7 days. To a control group, a microemulsion containing no test drug was administered in the same manner. Blood was collected in the presence of heparin sodium from the ear vein of each rabbit at 3 hours after the last administration. The blood was centrifuged at 2000 g for 10 minutes to separate plasma. The plasma was applied to electrophoresis using Paragon Electrophoresis System (Beckman Coulter, Inc.) to separate plasma lipoprotein, followed by lipid staining. The images on the gel after the lipid staining were examined to covert the plasma HDL level of each rabbit into a digitized form for the evaluation. In reference to the content amount of each compound in the microemulsion, each blood compound level assumed just after the intravenous administration thereof was set as the dose of each compound.

<Results>

As shown in Table 4, it was observed that the plasma HDL levels in rabbits administered with test drugs were increased about 1.5 to 1.9 times for probucol spiroquinone, about 1.3 to 1.4 times for probucol diphenoquinone, and about 1.3 to 1.4 times for probucol bisphenol, respectively, compared with that in control group.

TABLE 4

| Assayed Compound | Plasma HDL Level (Relative Ratio %) (Blood Level: $\mu$M) | |
| --- | --- | --- |
| Control (Non-treated) | 100 | |
| Probucol spiroquinone | 157 (0.14) | 194 (0.57) |
| Probucol diphenoquinone | 148 (0.16) | 130 (0.31) |
| Probucol bisphenol | 145 (0.14) | 135 (0.57) |

Assay Example 5

Toxicity Test

Probucol spiroquinone, probucol diphenoquinone, and probucol bisphenol were orally administered to mice for one week. As a result, it was verified that no abnormal findings were observed.

As shown above, it was confirmed that the ABCA1 stabilizer of the present invention provides the continuous and stable expression of ABCA1 without using genetic engineering techniques and accelerates the HDL-generating reaction, thereby acting as a prophylactic/therapeutic agent for low-HDL cholesterolemia. The active ingredients, the bisphenol-type compounds, according to the present invention have activity of elevating blood HDL levels, and hence are expected to have activity of modifying the cholesterol reverse-transport system to a preferable direction.

Formulation Example 1

According to the present invention, probucol spiroquinone: 200 mg, lactose: 100 mg, corn starch: 28 mg, and magnesium stearate: 2 mg The ingredients of the prescription above were formulated into capsules according to a known method specified in The Japanese Pharmacopoeia XIV, General Rules for Preparations.

Formulation Example 2

According to the present invention, probucol spiroquinone (25 mg) was dissolved in an aqueous isotonic solution of distilled water for injection (10 mL) containing an appropriate amount of sodium chloride. The resulting mixture was dispensed in each ampule, and then subjected to sterilization after sealing to obtain injections.

INDUSTRIAL APPLICABILITY

The ABCA1 stabilizers each containing an effective amount of a bisphenol-type compound selected from probucol spiroquinone, probucol diphenoquinone, and probucol bisphenol according to the present invention give the continuous and stable expression of ABCA1 without using complicated genetic engineering techniques. The ABCA1 stabilizers are effective drugs for various diseases such as low-HDL cholesterolemia and arteriosclerosis caused by a decrease in the ABCA1 expression. In addition, the ABCA1 stabilizers of the present invention utilize a metabolite of probucol which has already been assured to be pharmaceutically safe, and thus are useful as drugs because of their safety. Similarly, the effective ingredients can be used as agents for increasing the ABCA1 level and accelerating the HDL-generating reaction in vivo; increasing the blood level of HDL; activating the blood cholesterol reverse-transport pathway which takes up cholesterol from peripheral tissues; and/or suppressing the degradation of ABCA1 and accelerating in vivo HDL formation, and further can be used for prophylactic/preventive treatment of various diseases or abnormal conditions (specifically, being associated with a decrease in the blood HDL level).

While the present invention has been described specifically in detail with reference to certain embodiments and examples thereof, it would be apparent that it is possible to practice it in other forms. In light of the disclosure, it will be understood that various modifications and variations are within the spirit and scope of the appended claims.

What is claimed is:

1. A method for increasing expression of ATP-binding Cassette Transport 1 (ABCA1) comprising administering an effective amount of probucol spiroquinone or probucol diphenoquinone to a patient with low-HDL cholesterolemia or arteriosclerosis.

2. The method for increasing expression of ABCA1 according to claim 1, wherein the probucol spiroquinone or probucol diphenoquinone is administered in combination with at least one drug selected from the group consisting of antidiabetes drugs, therapeutic drugs for complications of diabetes, antiobesity drugs, antihypertensive drugs, antihyperlipidemic drugs, diuretics, antithrombotic drugs, and anti-Alzheimer's disease drugs.

* * * * *